United States Patent
Gheorghiu et al.

(10) Patent No.: US 11,680,939 B2
(45) Date of Patent: Jun. 20, 2023

(54) SYSTEMS AND METHODS FOR DETECTING BIOACTIVE COMPOUNDS USING SENSORS WITH PRE-STIMULATED CELLS

(71) Applicant: Centrul International de Biodinamica, Buchare (RO)

(72) Inventors: Mihaela Gheorghiu, Buchare (RO); Eugen Gheorghiu, Buchare (RO)

(73) Assignee: Centrul International de Biodinamica, Buchare (RO)

( * ) Notice: Subject to any disclaimer, the term of this patent is extended or adjusted under 35 U.S.C. 154(b) by 994 days.

(21) Appl. No.: 16/440,789

(22) Filed: Jun. 13, 2019

(65) Prior Publication Data
US 2019/0383791 A1 Dec. 19, 2019

(51) Int. Cl.
*G01N 33/487* (2006.01)
*G01N 33/50* (2006.01)
*G01N 27/02* (2006.01)
*G01N 27/327* (2006.01)

(52) U.S. Cl.
CPC ..... *G01N 33/48728* (2013.01); *G01N 27/021* (2013.01); *G01N 33/5041* (2013.01); *G01N 27/3273* (2013.01)

(58) Field of Classification Search
CPC ......... G01N 33/48728; G01N 33/5041; G01N 33/4836; G01N 27/021; G01N 27/026; G01N 27/3273; G01N 27/327–3278
See application file for complete search history.

(56) References Cited

U.S. PATENT DOCUMENTS

| 5,187,096 A | 2/1993 | Giaever et al. |
| 6,280,586 B1 | 8/2001 | Wolf et al. |
| 6,377,057 B1 | 4/2002 | Borkholder |
| 9,612,234 B2 | 4/2017 | Li et al. |

(Continued)

FOREIGN PATENT DOCUMENTS

| EP | 2631652 A1 | 8/2013 | |
| WO | WO-2005077104 A2 * | 8/2005 | ............ C12M 25/08 |
| WO | WO-2017192579 A1 * | 11/2017 | ........... C12N 5/0657 |

OTHER PUBLICATIONS

Bennet, D. and Kim, S., Impedance-based cell culture platform to assess light-induced stress changes with antagonist drugs using retinal cells. Analytical chemistry, 85(10), pp. 4902-4911 (2013) (Year: 2013).*

(Continued)

*Primary Examiner* — J. Christopher Ball
(74) *Attorney, Agent, or Firm* — Law Office of Andrei D Popovici, PC

(57) ABSTRACT

Described systems and methods allow the detection and quantitation of a target analyte such as a toxin, drug, pesticide, etc. Some embodiments use a sensor comprising photo-sensitive cells, e.g., cells genetically modified to express an opsin. A light source such as an LED is used to optically stimulate the sensor cells, triggering changes in a measurable quantity such as the polarization of the cell membrane. Some embodiments use electrical impedance measurements to monitor the cell's recovery from the state induced by the optical stimulation. The recovery process is affected by the presence of certain bio-active compounds, which allows detection and quantitation of such compounds.

20 Claims, 9 Drawing Sheets

(56) References Cited

U.S. PATENT DOCUMENTS

2012/0208283 A1* 8/2012 Gheorghiu ......... G01N 35/0098
 422/82.01
2016/0178628 A1 6/2016 Abdolahad et al.

OTHER PUBLICATIONS

Bennet, D., Kim, M.G. and Kim, S., Light-induced anatomical alterations in retinal cells. Analytical biochemistry, 436(2), pp. 84-92 (2013).*

Banerjee et al., "Mammalian cell-based biosensors for pathogens and toxins", Trends in Biotechnology, vol. 27, No. 3, pp. 179-188, Mar. 2009.

Behm et al., "Cytotoxic Potency of Mycotoxins in Cultures of V79 Lung Fibroblast Cells", Journal of Toxicology and Environmental Health, Part A: Current Issues, vol. 75, Issue 19-20, pp. 1226-1231, published online Sep. 20, 2012.

Ceriotti et al., "Assessment of cytotoxicity by impedance spectroscopy", Biosensors and Bioelectronics, vol. 22, Issue 12, pp. 3057-3063, Jun. 15, 2007.

Gheorghiu et al., "Label free sensing platform for amyloid fibrils effect on living cells", Biosensors and Bioelectronics, vol. 52, pp. 89-97, Feb. 15, 2014.

Giaever et al., "Monitoring fibroblast behavior in tissue culture with an applied electric field", Proc. Natl. Acad. Sci. USA, vol. 81, pp. 3761-3764, Jun. 1984.

Kintzios et al., "Bioelectric recognition assay (BERA)", Biosensors & Bioelectronics, vol. 16, pp. 325-336, Jul. 2001.

Liu et al., "Detection of heavy metal toxicity using cardiac cell-based biosensor", Biosensors and Bioelectronics, vol. 22, Issue 12, pp. 3224-3229, Jun. 15, 2007.

Rider et al., "A B Cell-Based Sensor for Rapid Identification of Pathogens", www.sciencemag.org, Science, vol. 301, Issue 5630, pp. 213-215, Jul. 11, 2003.

Tarantola et al., "Cytotoxicity of Metal and Semiconductor Nanoparticles Indicated by Cellular Micromotility", ACS Nano, vol. 3, No. 1, pp. 213-222, published online Dec. 18, 2008.

Gheorghiu, U.S. Appl. No. 16/438,866, filed Jun. 12, 2019.

* cited by examiner

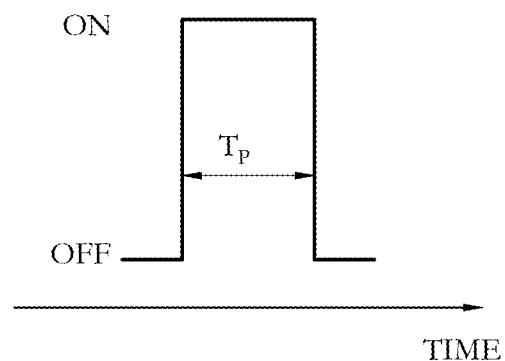
FIG. 3-A
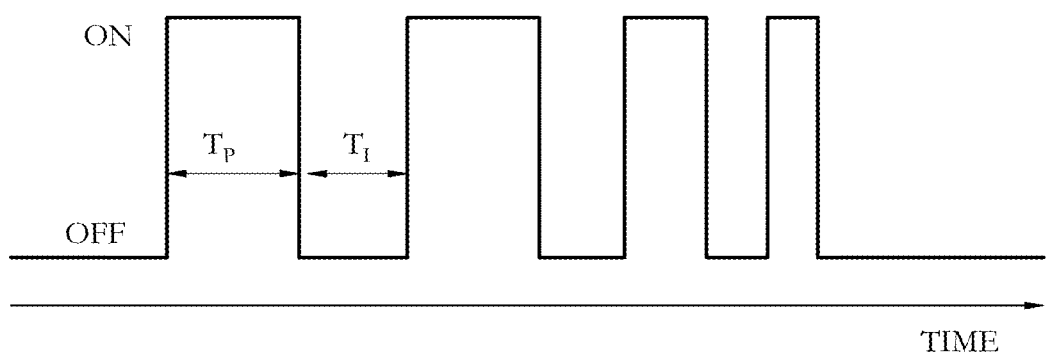
FIG. 3-B

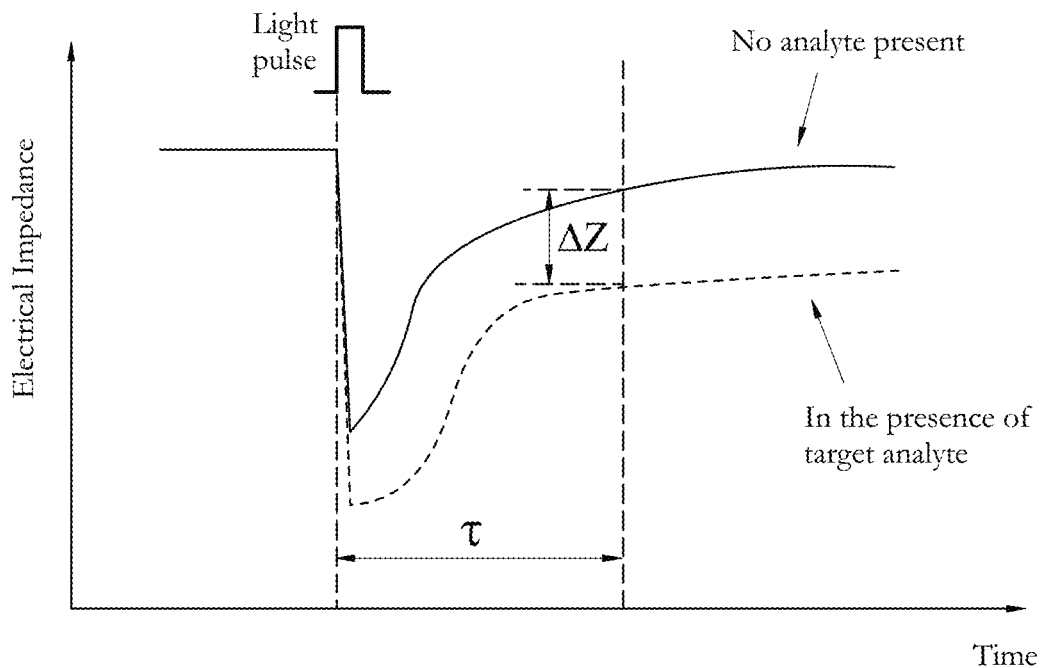
FIG. 4-A
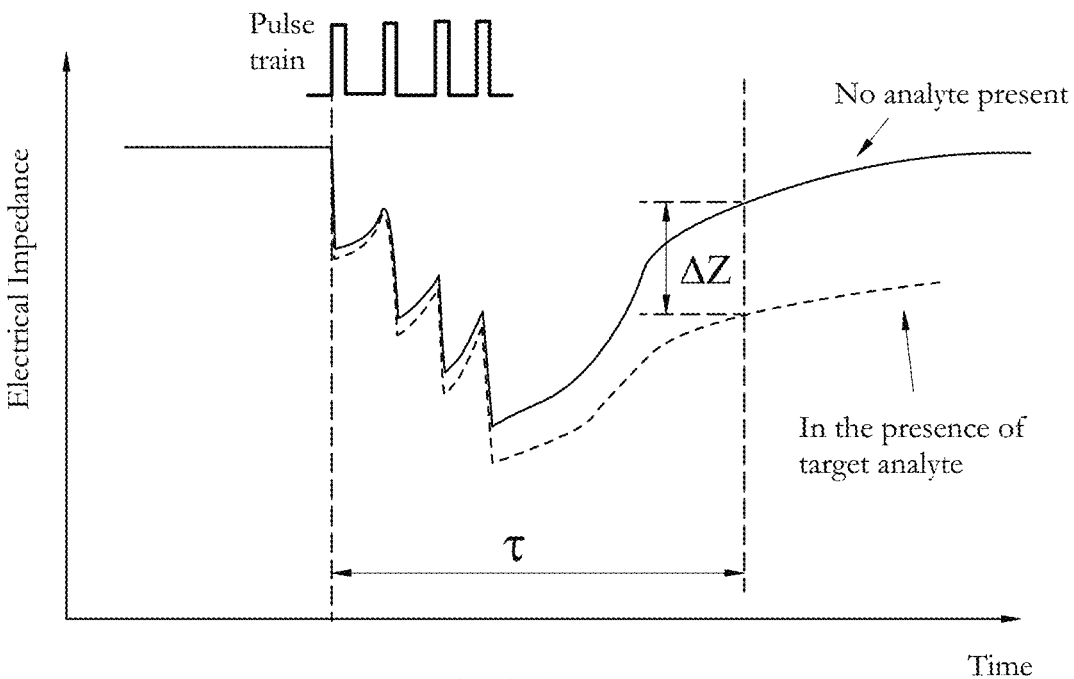
FIG. 4-B

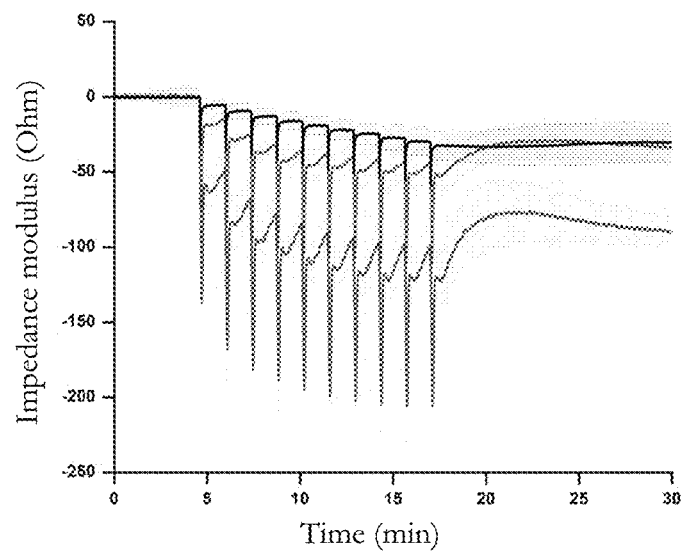
FIG. 8-A
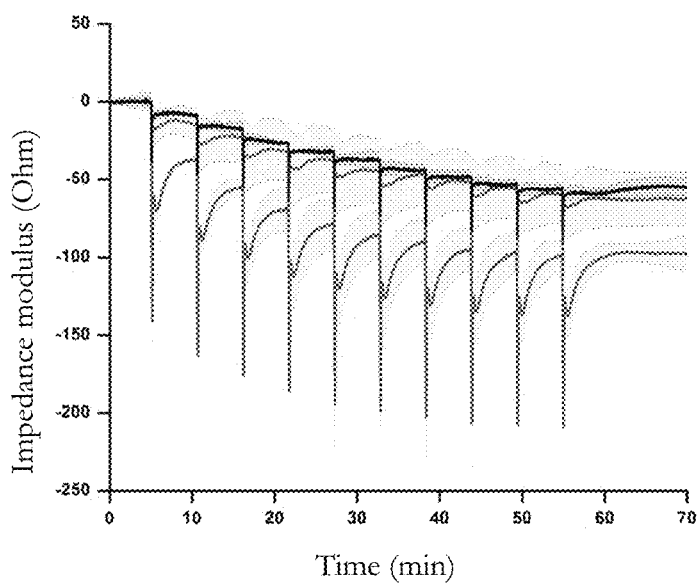
FIG. 8-B

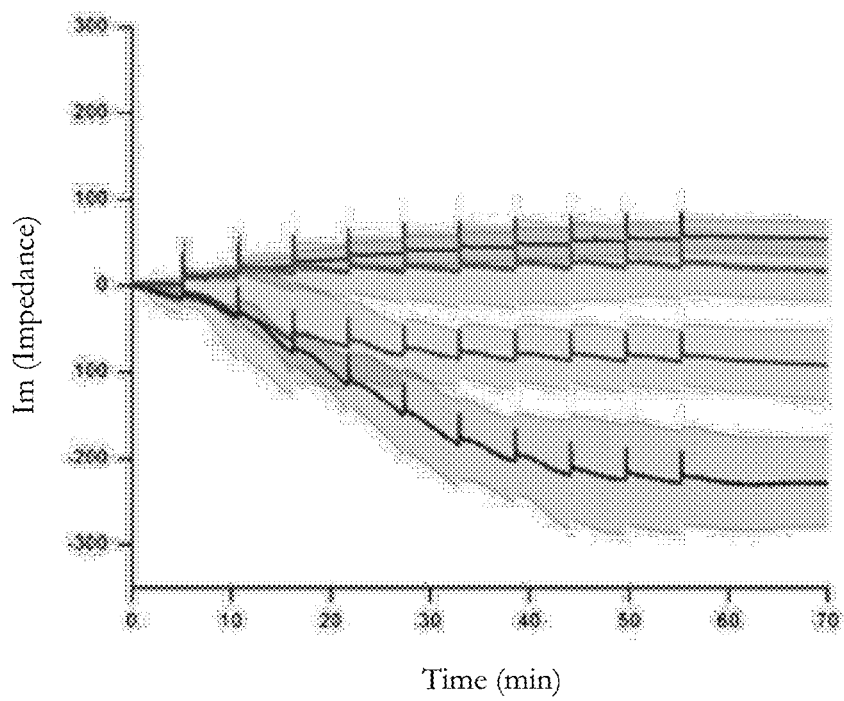
FIG. 10-A
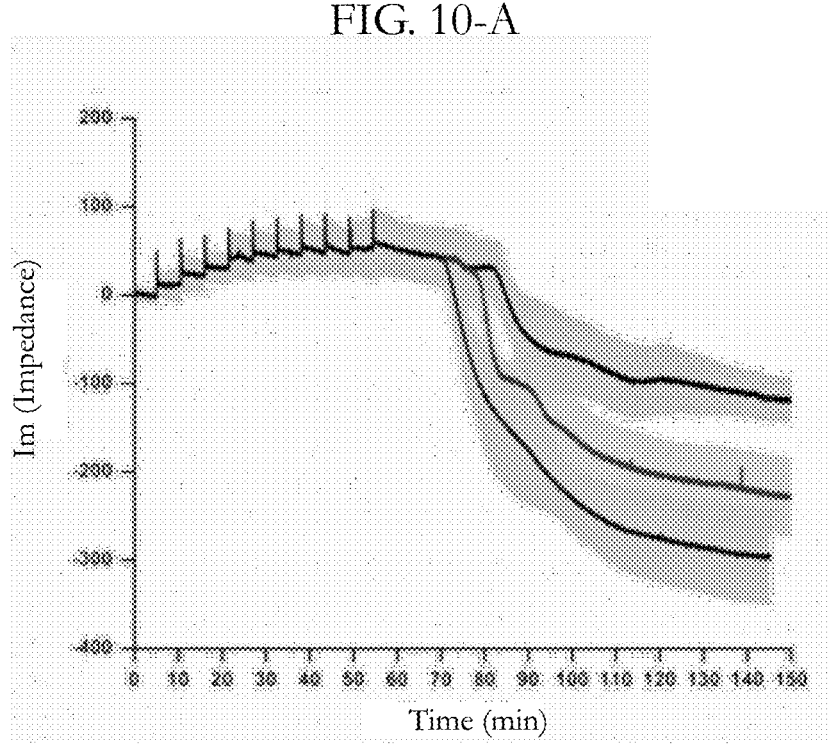
FIG. 10-B

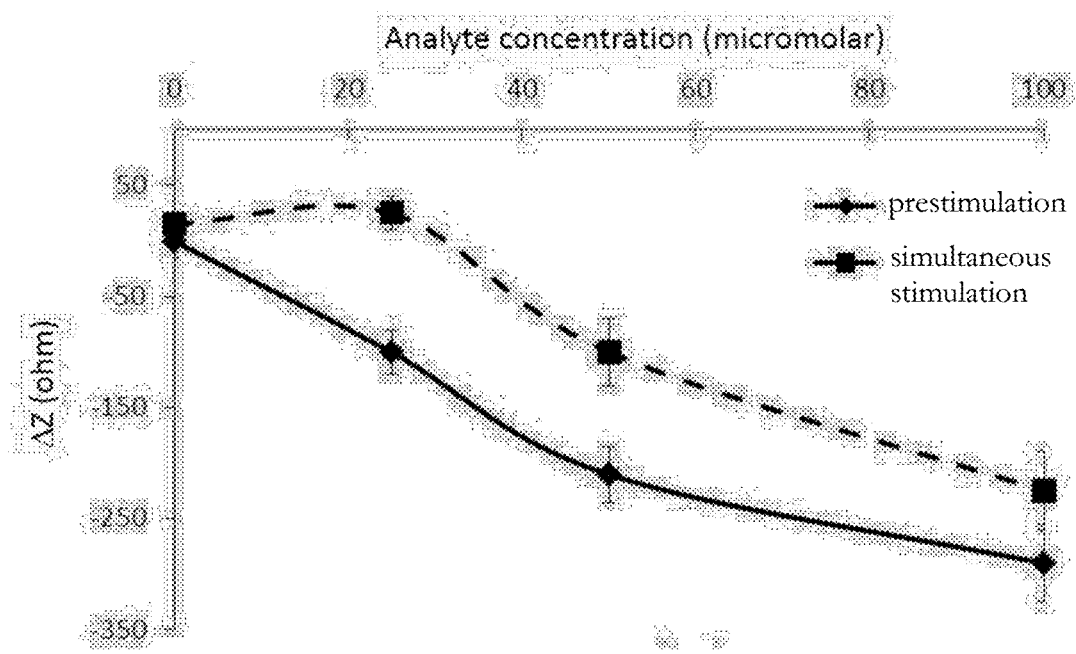
FIG. 11-A
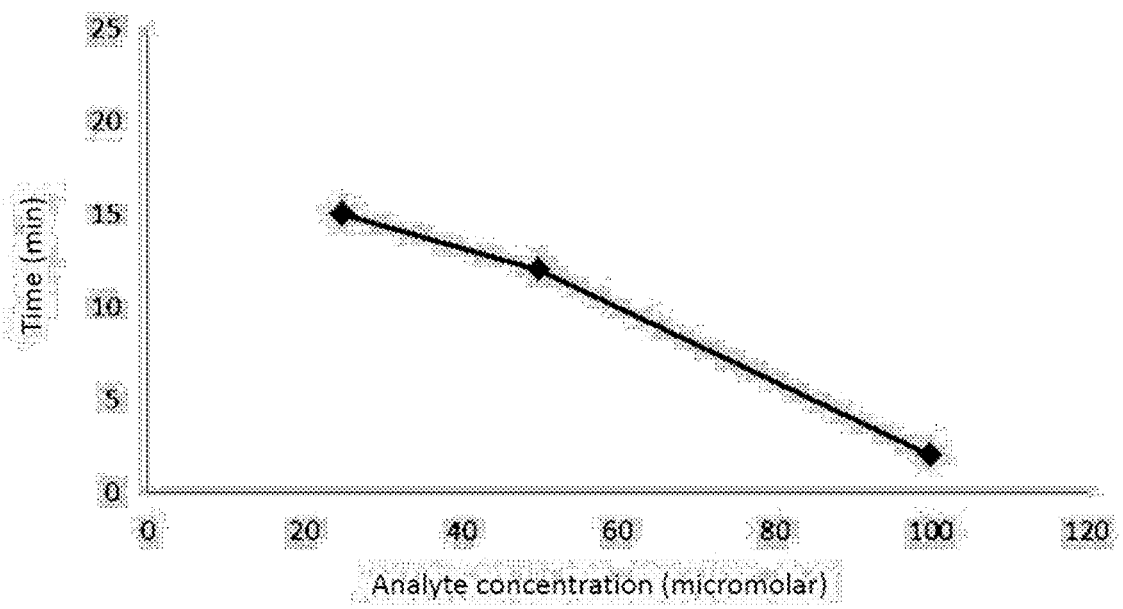
FIG. 11-B

SYSTEMS AND METHODS FOR DETECTING BIOACTIVE COMPOUNDS USING SENSORS WITH PRE-STIMULATED CELLS

CROSS-REFERENCE TO RELATED APPLICATIONS

This application claims priority to Romanian patent application Ser. A/00420/2018, by M. Gheorghiu et al., filed on Jun. 13, 2018, which is incorporated herein by reference.

BACKGROUND

The invention relates to biosensing and immunoassay systems and methods.

Methods of detecting the presence of an analyte in solution, as well as of determining a response of living cells to an exposure to such analytes have been receiving attention worldwide. Such methods may have the sensitivities and specificities required by applications in medicine, as well as in the food and pharmaceutical industries. Target analytes of particular interest comprise biological cells such as bacteria, and also analytes of comparatively lower molecular weight such as viruses, DNA fragments, as well as toxins, drugs, pesticides, herbicides, heavy metals, etc.

Several examples of using living cells (e.g., cardiomyocytes, lymphocytes, epithelial cells, fibroblasts) as bioreceptors/biosensors are known in the art. Typical examples use optical analytical methods (e.g., surface plasmon resonance—SPR), thermal methods (calorimetry), or electrical (e.g., impedance or electrophysiological measurements) to evaluate the cellular response caused by exposure to a target analyte according to the effect the respective analyte has on cell adhesion, signaling, growth rate, etc.

One such example, European Patent No. 2,631,652 A1 describes compositions and methods for cellular analyses using optical biosensors (e.g., SPR) without contrast agents. Such methods and systems have the disadvantage of a limited specificity, since the same type of effect is visible for a large class of compounds. In turn, U.S. Pat. No. 6,377,057 B1 describes the use of spectral density of induced changes in cellular electrical potential for the classification of biologically active agents. Some disadvantages of such methods and systems include a susceptibility to cellular variability and a reliance on reference compounds, which may make such methods difficult to automate.

The monitoring of adherent cells via electrical impedance measurements has proved useful in various environmental, chemical, and pharmaceutical applications. For instance, there exist commercial electrode systems as described in U.S. Pat. No. 5,187,096. US Pre-grant Publication No. 2016/0178628 A1 discloses a method for detecting and monitoring cell attachment to an electric cell-substrate impedance sensing (ECIS) electrode for cancer diagnosis. U.S. Pat. No. 6,280,586 B1 shows a sensing device that uses biological cells or other biologically active chemicals, coupled with electrical measurements at a porous electrode to which the sensing cells are adhered. Some disadvantages of such systems and methods include a reliance on relatively slow cellular response processes (of the order of days), and a reliance on cells specifically modified for a target analyte type.

Considering the drawbacks of conventional biosensing systems and methods, there is considerable interest in developing new methods and systems using living cells as biosensors for detection and quantitation of target analytes in medical, food science, pharmaceutical, and environmental applications.

SUMMARY

According to one aspect, the present invention comprises a method of processing measurements of an electrical impedance of a sensor contained within a measurement chamber, the measurement chamber configured to receive a target sample. The sensor comprises a culture of photosensitive living cells attached to a surface of the sensor. The method comprises employing a light source to deliver a pulse of light to the sensor. The method further comprises, in response to delivering the pulse of light to the sensor, employing an electrical impedance analyzer to acquire an impedance response time series comprising a plurality of values, wherein each value of the plurality of values is determined according to a measured electrical impedance of the sensor, and wherein at least two values of the plurality of values are determined at distinct time instances. The method further comprises, in response to acquiring the impedance response time series, determining whether the target sample comprises a target analyte according to the impedance response time series.

According to another aspect, a system comprises a sensor contained within a measurement chamber, the sensor comprising a culture of photosensitive living cells attached to a surface of the sensor. The system further comprises a light source configured to illuminate the sensor, and a computer system connected to the light source and to an electrical impedance analyzer configured to measure an electrical impedance of the sensor. The computer system comprises at least one hardware processor configured to actuate the light source to deliver a light pulse to the sensor. The at least one hardware processor is further configured, in response to delivering the light pulse, to actuate the electrical impedance analyzer to acquire an impedance response time series comprising a plurality of values, wherein each value of the plurality of values is determined according to a measured electrical impedance of the sensor, wherein at least two values of the plurality of values are determined at distinct time instances. The at least one hardware processor is further configured, in response to the acquisition of the impedance response time series, to determine whether the target sample comprises a target analyte according to the impedance response time series.

BRIEF DESCRIPTION OF THE DRAWINGS

The foregoing aspects and advantages of the present invention will become better understood upon reading the following detailed description and upon reference to the drawings where:

FIG. 3-A illustrates an exemplary light pulse according to some embodiments of the present invention.

FIG. 3-B illustrates an exemplary pulse train according to some embodiments of the present invention.

FIG. 4-A shows an exemplary change of a sensor impedance caused by a light pulse according to some embodiments of the present invention.

FIG. 4-B shows an exemplary impedance response of a sensor caused to a train of light pulses according to some embodiments of the present invention.

FIG. 8-A shows an exemplary set of experimental impedance response measurements performed with pulse trains having relatively short inter-pulse intervals.

FIG. 8-B shows an exemplary set of experimental impedance response measurements performed with pulse trains having relatively long inter-pulse intervals.

FIG. 10-A illustrates a set of exemplary response curves determined for varying concentrations of a target analyte, measured experimentally according to some embodiments wherein light pulses are applied following injection of the target analyte.

FIG. 10-B illustrates another set of exemplary response curves determined for varying concentrations of a target analyte, measured experimentally according to some embodiments wherein light pulses are applied before injection of the target analyte.

FIG. 11-A shows an exemplary calibration curve allowing a quantitation of a detected analyte according to some embodiments of the present invention.

FIG. 11-B shows another exemplary calibration curve allowing quantitation of a detected analyte according to some embodiments of the present invention.

DETAILED DESCRIPTION OF PREFERRED EMBODIMENTS

In the following description, it is understood that all recited connections between structures can be direct operative connections or indirect operative connections through intermediary structures. A set of elements includes one or more elements. Any recitation of an element is understood to refer to at least one element. A plurality of elements includes at least two elements. Unless otherwise required, any described method steps need not be necessarily performed in a particular illustrated order. A first element (e.g. data) derived from a second element encompasses a first element equal to the second element, as well as a first element generated by processing the second element and optionally other data. Making a determination or decision according to a parameter encompasses making the determination or decision according to the parameter and optionally according to other data. Unless otherwise specified, an indicator of some quantity/data may be the quantity/data itself, or an indicator different from the quantity/data itself. It is generally understood that values of the electrical impedance are complex numbers. However, the term impedance is herein used generically to represent any of a complex impedance, a real part of an impedance, an imaginary part of an impedance, and a modulus of an impedance.

The following description illustrates embodiments of the invention by way of example and not necessarily by way of limitation.

Figure 1:
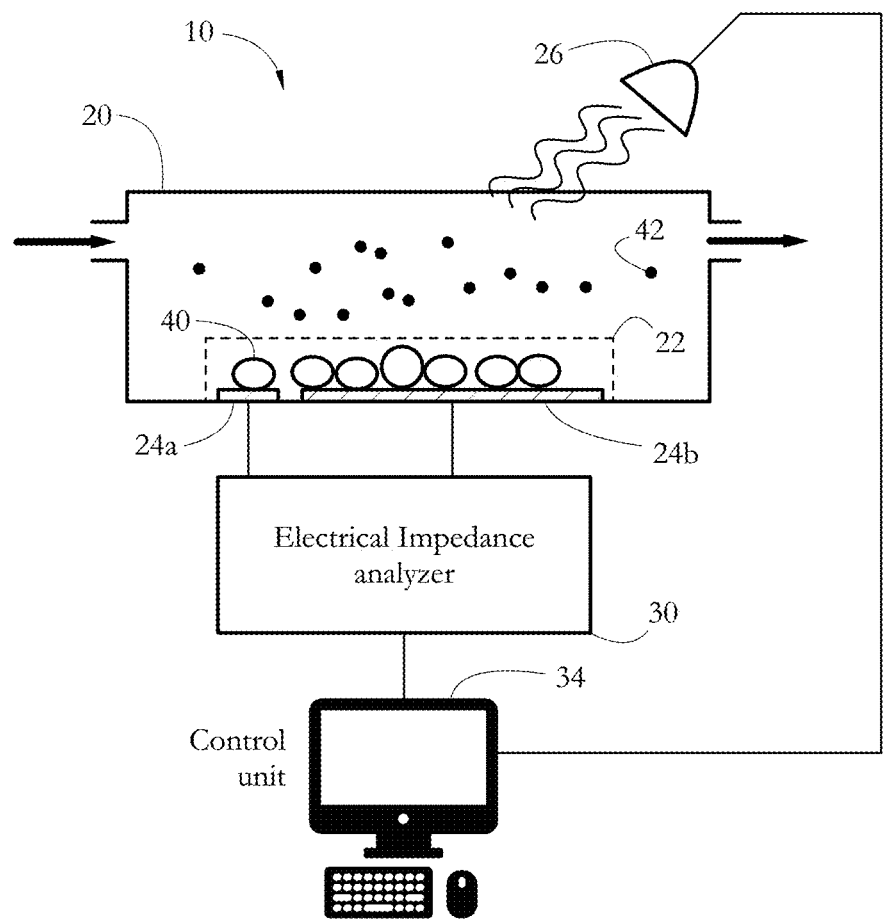
FIG. 1 shows a diagram of an exemplary measurement system according to some embodiments of the present invention.

FIG. 1 shows a diagram of an exemplary measurement system 10 for detecting and/or quantitating a target analyte according to some embodiments of the present invention. System 10 comprises a measurement chamber 20, a stimulation lamp 26, an electrical impedance (EI) analyzer 30, and a control unit 34 connected to the EI analyzer and lamp 26. System 10 may further comprise a sample reservoir, a pump or syringe for flushing the measurement chamber and for injecting a target sample, fluid lines, and other auxiliary equipment which was omitted for simplicity. Chamber 20 and lamp 26 may be placed together in a sealed enclosure that provides controlled experimental conditions (e.g., temperature, humidity, concentration of various gases).

Measurement chamber 20 further comprises a sensor 22 comprising an electrical transducer (e.g., glass plate comprising a pair of planar electrodes 24a-b) connected to EI analyzer 30. An alternative sensor may comprise an optical transducer, for instance as used in surface plasmon resonance measurements. Sensor 22 further comprises a set of living cells 40 attached to a solid surface of the sensor, preferably in the vicinity of the electrode pair so as to facilitate impedance measurements. Sensor cells may be cultured directly on the surface of the electrical transducer according to a culture protocol that encourages attachment to and coating of the electrodes.

Measurement chamber 20 is further configured to receive a liquid sample which may contain a target analyte 42. The sample may be introduced in a static or flow configuration. Exemplary target analytes include various chemical substances e.g., antibiotics, toxins, polypeptides, hormones, pesticides, drugs (e.g., chemotherapy pharmaceuticals), drug residues, etc., susceptible of inducing changes in some vital parameter of the living sensor cells. For instance, target analytes may induce changes in the properties of the cellular membrane, or even the death of the target cell. Such changes may be indirectly detected by measuring changes in some physical property (e.g., impedance, index of refraction) of the sensor, as shown in more detail below.

Stimulation lamp 26 comprises a light-emitting device used for stimulating the sensor cells as shown in more detail below. Exemplary stimulation lamps include a discharge lamp, a light-emitting diode (LED), and a laser source, among others. Lamp 26 may emit in a broad or a narrow band of wavelengths. The wavelength of emitted electromagnetic radiation may be specifically chosen according to a receptivity profile of sensor cells. In an exemplary embodiment, lamp 26 comprises an LED emitting a narrow band of wavelengths around 470 nm. Alternatives to stimulation lamp 26 comprise devices delivering an electrical, chemical, or mechanical stimulation to sensor 22.

In some embodiments, EI analyzer 30 includes an alternating current (AC) generator, an amplifier, and a signal processing unit. In some embodiments, the AC generator produces a high frequency sinusoidal voltage with a range of amplitudes, e.g., 20 µV-2 mV, and a range of measurement frequencies such as 1-500 kHz, which is applied to electrodes 24a-b of sensor 22. The applied voltage enables a measurement of the electrical impedance of electrodes 24a-b. The measured electrical signal is amplified and/or filtered by the amplifier and fed into the signal processing unit, which may further convert the signal into a digital form, and transmit the digital form to control unit 34, e.g. through a serial communication interface.

Control unit 34 may be a computer system configured to control/actuate stimulation lamp 26, to receive data from EI analyzer 30, and to determine whether the sample contained in measurement chamber 20 comprises the target analyte according to impedance time series, as described below. In some embodiments, control unit 34 may be further configured to determine a concentration of the target analyte. Control unit 34 may further communicate detection/quantitation results to a human operator and/or to output such results in data form. Control unit 34 comprises a processor (e.g. a microprocessor, a multi-core integrated circuit formed on a semiconductor substrate, etc.) configured to execute computational and/or logical operations with a set of signals and/or data, such as data provided by EI analyzer 30. Such operations may be encoded in the form of a sequence of processor instructions, e.g., machine code. Control unit 34 further comprises volatile computer-readable media (e.g. DRAM, SRAM) storing instructions and/or data accessed or generated by the processor, input devices (e.g., keyboard, communication interfaces for receiving signal/data) and/or output devices (e.g., display) for communicating data to a human operator.

Figure 2:
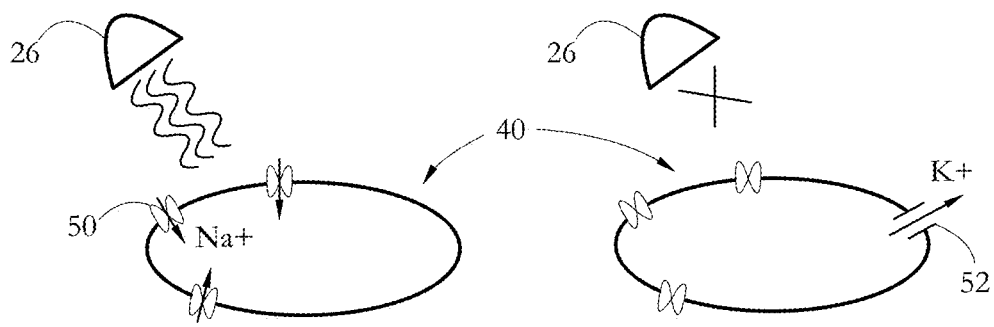
FIG. 2 illustrates an exemplary behavior of sensor cells when exposed to light according to some embodiments of the present invention.

FIG. 2 illustrates an exemplary behavior of sensor cells when exposed to light according to some embodiments of the present invention. Some embodiments employ sensor cells which are genetically modified to express an opsin (e.g., channel rhodopsin, without loss of generality), and/or other channel proteins with a role in maintaining cellular homeostasis (e.g., potassium channel ROMK1, without loss of generality). In the illustrated example, exposure to light induces a sudden intake of sodium ions through the cell membrane, which may substantially change the membrane potential and therefore the measured impedance of the respective cell. When the electromagnetic stimulation is turned off, ion exchange via the potassium channel progressively repolarizes the cell membrane, restoring the respective cell to its natural unperturbed state, or at least to a state which is closer to homeostasis than immediately following electromagnetic stimulation.

Some embodiments deliver electromagnetic stimulation to sensor cells in the form of light pulses. FIGS. 3-A-B illustrates a single pulse and a pulse train, respectively, according to some embodiments of the present invention. Pulses may have adjustable parameters such as a pulse intensity, a pulse duration $T_p$ and an inter-pulse interval $T_I$. Pulse trains comprise a plurality of individual (possibly non-identical) pulses in quick succession. Some embodiments may allow varying the count of pulses within a pulse train.

FIGS. 4-A-B show exemplary impedance responses of a sensor to a single light pulse and to a pulse train, respectively, according to some embodiments of the present invention wherein the sensor is prepared to contain cells having optically-sensitive ion channels. As the cellular membrane potential changes in response to the light pulse(s), the change is registered in the measured impedance of the sensor. Successive application of multiple pulses (pulse train, FIG. 4-B) may have a cumulative effect on impedance. When the light is turned off, a relatively slower process of repolarization restores the sensor impedance to a value closer to the baseline. The kinetics of recovery may depend on the characteristic response to the optical stimulation, but also on the effect of a bio-active target analyte on the cell membrane. Stated otherwise, the presence of a bio-active compound (e.g., toxin, drug) in the environment of the cell may substantially change the ability of the cell to recover from the stimulated state. As seen in FIGS. 4-A-B, the impedance response of the sensor under the influence of a target analyte differs from the impedance response in the absence of the respective analyte. This observation enables some embodiments of the present invention to detect and/or quantitate the target analyte from time series of impedance measurements.

Figure 5:
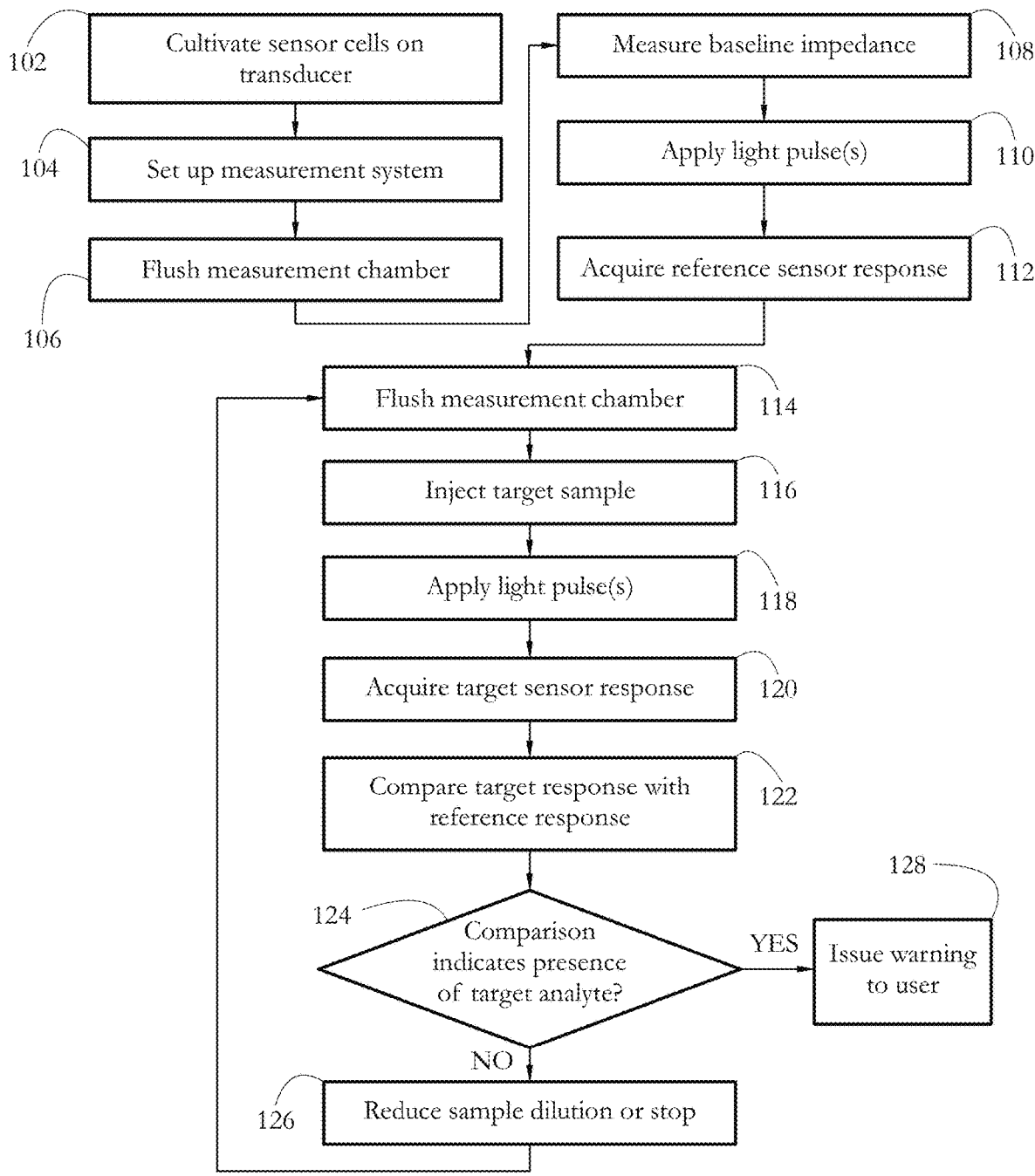
FIG. 5 shows an exemplary sequence of steps carried out to detect the presence of a target analyte in a sample according to some embodiments of the present invention.

FIG. 5 shows an exemplary sequence of steps performed to detect the presence in the sample of a target analyte according to some embodiments of the present invention. After preparing sensor 22 by cultivating the sensor cells, introducing the sensor to the measurement chamber and flushing the chamber with neutral solution (i.e., not contaminated with the target analyte), a step 108 determines a baseline impedance of sensor 22. The baseline value may be used to eliminate measurement drift, as well as to verify that the sensor is in good working order at later times. Steps 110-112 then apply a set of light pulses to the sensor and acquires a reference impedance response time series. Data acquisition may take place during illumination, as well as after the light stimulus is turned off. Impedance measurements may be performed at a fixed frequency (e.g., 1 kHz) or within a broader frequency range (e.g., 100 Hz-100 kHz).

Impedance response time series comprise a plurality of values, at least two of which are determined at distinct moments in time. A typical impedance response time series may comprise, for instance, one impedance value measured every second, for the duration of a few minutes to one hour. Each value is determined according to a real measurement of the impedance of sensor 22, the measurement performed at the respective time. Exemplary values of the impedance response may comprise a modulus of the measured impedance, a real part of the measured impedance, and an imaginary part of the measured impedance. In some embodiments, values of the impedance response time series are shifted and/or rescaled so they do not necessarily represent real measured values. Instead, they may represent, for instance, departures of the measured impedance from a pre-determined baseline value (see step 108).

Once a reference impedance response time series has been acquired, some embodiments store the reference time series on computer-readable media of control unit 34 and use the stored reference data for subsequent measurements. Next, a target fluid sample is introduced into measurement chamber 20. In a step 118, control unit 34 actuates stimulation lamp 26 to apply a set of light pulses to the sensor. In some embodiments, pulse(s) applied in step 118 have the same characteristics (intensity, count of pulses, pulse width, pulse interval) as the one(s) applied during determination of the reference impedance time series.

A step 120 acquires a target impedance time series comprising a plurality of values, at least two of which are determined at distinct moments in time. Each value of the target impedance time series is determined according to a measured value of the impedance of sensor 22 determined at the respective time. In some embodiments, the reference and target impedance response time series are acquired at the same time intervals relative to the start of the optical stimulation. For instance, if the reference time series consists of values $\{Z^R_1, Z^R_2, \ldots, Z^R_n\}$ measured at time instances $\{t^R_1, t^R_2, \ldots, t^R_n\}$, respectively, and the target time series consists of values $\{Z^T_1, Z^T_2, \ldots, Z^T_n\}$, measured at instances $\{t^T_1, t^T_2, \ldots, t^T_n\}$, respectively, and if light stimulation started at moment $r^R_0$ for the reference time series and $t^T_0$ for the target time series, then $t^T_1 - t^T_0 \approx t^R_1 - t^R_0$, $t^T_2 - t^T_0 \approx t^R_2 - t^R_0$, etc.

Next, a step 122 performs a comparison between the target and reference time series. In some embodiments, step 122 comprises determining a measure of similarity between the two sets of impedance response values. For instance, a measure of similarity may be determined according to:

$$D = \sum_{k=1}^{n}(Z_k^T - Z_k^R),\quad [1]$$

which uses the notation developed above.

In some embodiments, the measure of similarity comprises a difference between a selected value of the target time series and a selected value of the reference time series, both said selected values determined at approximately the same time after the start of their respective optical stimulation. For instance, by reference to FIGS. 4-A-B, such a similarity measure may amount to determining a distance $\Delta Z$ between the target and reference response curves at a pre-determined time $\tau$ following the start of the optical stimulation. The value of the delay $\tau$ may be determined according to various criteria and/or through experimentation. For instance, some embodiments determine $\tau$ according to a signal-to-noise ratio of impedance measurements, the motivation being that the determined $\Delta Z$ should be larger than the measurement error to trigger detection of the target analyte. Alternatively, $\tau$ may be chosen according to a desired assay duration criterion. Typical $\tau$ values are of the order of a few minutes to one hour, and may depend on the type of sensing cell and/or target analyte.

In a step 124 the calculated similarity measure may be compared to a pre-determined threshold to determine whether the acquired impedance time series indicates a presence of the target analyte. When the reference time series is considered sufficiently similar to the target time series, a determination is made that there is no indication that the target analyte is present, in which case the analysis may stop. Alternatively, steps 114-126 may be re-run using a modified, more concentrated sample. When the reference and target time series are considered sufficiently dissimilar, a decision may be made that the sensor indicates the presence of the target analyte in the sample, in which case in a step 128, control unit 34 may display a warning to a human operator.

Some embodiments also determine an approximate concentration of the target analyte in the sample according to a measure of similarity between the target and reference time series (e.g., according to $\Delta Z$). Such determinations typically require a series of calibration measurements using samples of known concentrations of the target analyte. Exemplary calibration curves are shown, for instance in FIGS. 11-A-B.

The method described in FIG. 5 may be automated at least in part, i.e., may be executed by control unit 34 according to a computer program. Some method steps such as preparing the sample, injecting the target analyte, etc., may be executed by a human operator or may be automated, for instance by having control unit 34 actuate a pump.

Figure 6:
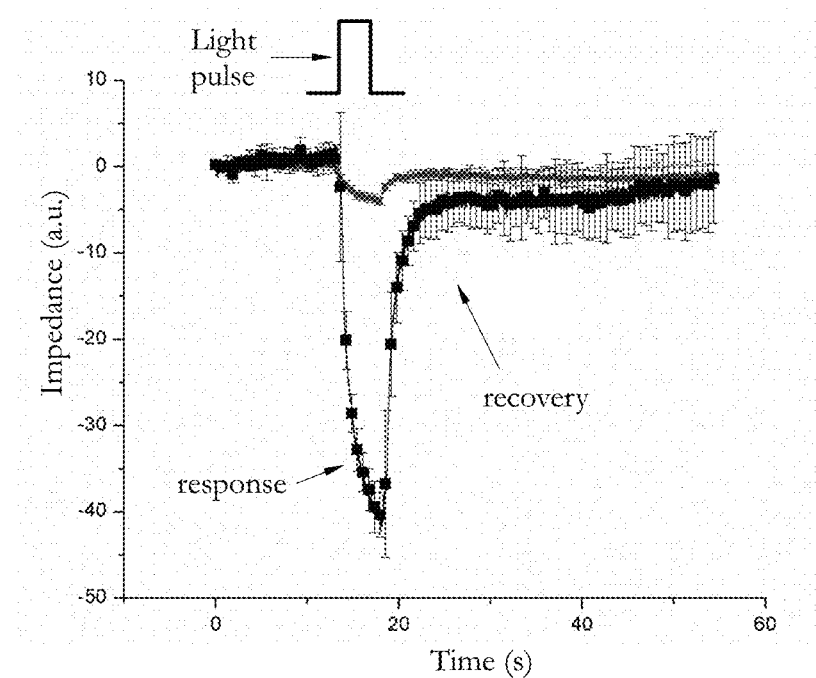
FIG. 6 shows an exemplary impedance response of a sensor to a light pulse, measured experimentally according to some embodiments of the present invention.
Figure 7:
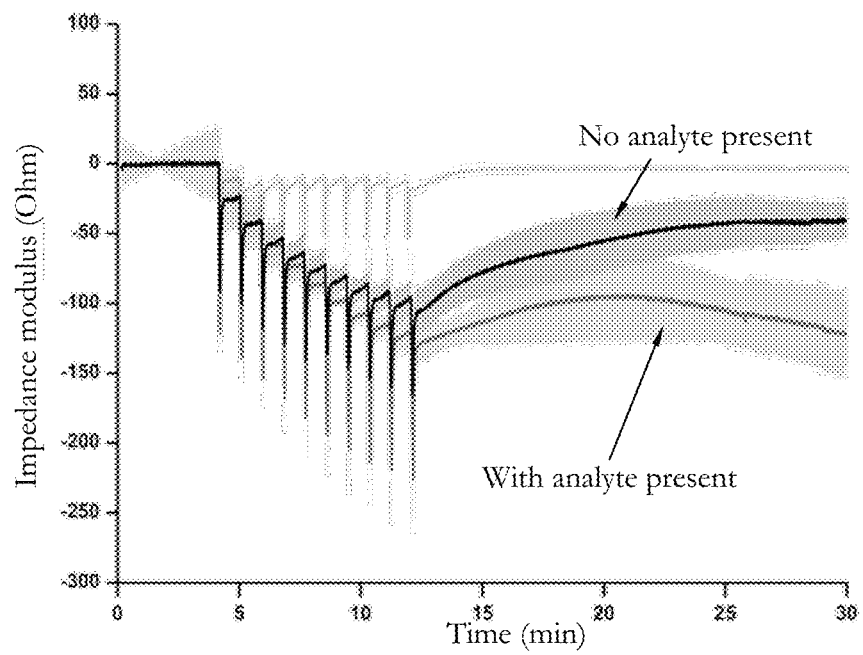
FIG. 7 shows an exemplary impedance response of a sensor in the absence and in the presence of a target analyte, respectively, measured experimentally according to some embodiments of the present invention.

FIGS. 6-11 illustrate actual experimental data (impedance response time series) obtained using some embodiments of the present invention. For instance, FIG. 6 shows an actual response of an embodiment of sensor 22 to a light pulse. The top data series corresponds to sensing cells which have are not photo-sensitive, while the bottom curve corresponds to sensing cells that have been genetically altered to express an opsin. FIG. 6 also shows a typical size of a measurement error (i.e., error bars) caused by noise. FIG. 7 shows actual impedance response time series measured in an embodiment, together with the respective error bars. In the example of FIG. 7, optical stimulation comprises a pulse train.

Figure 9:
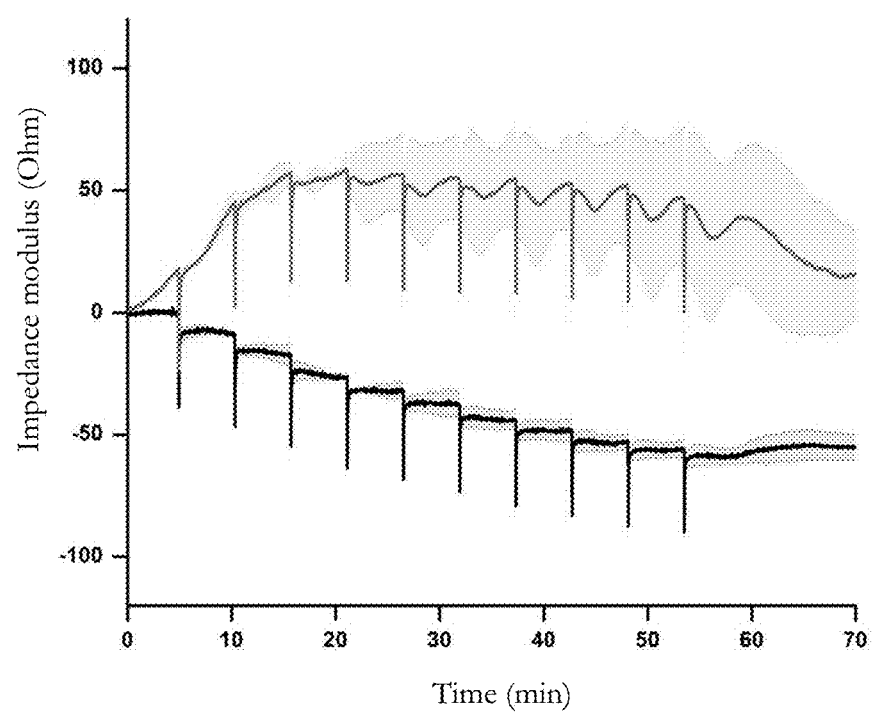
FIG. 9 shows an exemplary response of a sensor to exposure to a cytotoxin, measured experimentally according to some embodiments of the present invention.

FIG. 8-A shows optical stimulation with a pulse train, wherein the inter-pulse interval is relatively small. In contrast, the inter-pulse interval is much larger in the example of FIG. 8-B. FIG. 9 shows an exemplary response of a sensor to exposure to a cytotoxin (top curve vs. clean sample on the bottom), measured experimentally according to some embodiments of the present invention. The figure shows that the parameters of the membrane repolarization processes, bringing cells back to the physiological values, as well as the sign and magnitude of the response to applied pulses are dependent on the sensor cells homeostatic capacity (ionic and energetic). In the example of FIG. 9, the toxin ouabain is blocking the sodium potassium pump, with visible modifications of cell homeostasis.

The magnitude of the response of the sensor depends on the concentration of the target analyte, which allows some embodiments not only to detect the presence of the target analyte, but also to approximately determine its concentration. FIGS. 10-A-B show impedance response time series determined for samples having various concentrations of a heavy metal salt ($CdCl_2$ is a known cytotoxic). The concentration of the target analyte increases from top to bottom, respectively 0, 20, 50, and 100 µM.

FIGS. 10-A-B further show two distinct manners of stimulating sensor 22. Whereas in the example of FIG. 10-A the optical stimulation (light pulses) was applied while the target analyte is already in contact with the sensor (simultaneous stimulation), in the example of FIG. 10-B, the target analyte is brought in contact with a pre-stimulated sensor. Stated otherwise, the sensor is first optically stimulated, and the target analyte is brought into the measurement chamber at a later time. Some embodiments use the observed effect of sensitization of the sensor cells when pre-stimulated, which may make them significantly more responsive in the low concentration range (e.g., below 25 µM) as shown in FIG. 10-B.

FIGS. 11-A-B show different versions of calibrating curves derived from data shown in FIGS. 10-A-B. FIG. 11-A shows an example of a calibration curve based on a determination of $\Delta Z$, and FIG. 11-B shows an example of a calibration curve based on the time at which the target response time series departs from the baseline time series by more than the measurement error, said time measured with respect to the moment when the sample containing the cytotoxic compound is introduced into the measurement chamber.

The exemplary systems and methods described above allow detecting and quantifying a target analyte such as a toxin, drug, pesticide, etc. Some embodiments use a sensor comprising photo-sensitive cells, e.g., cells genetically modified to express an opsin. A light source such as an LED is used to stimulate the sensor cells, for instance by exposing them to a light pulse. Such stimulation produces changes in some physical property of the sensor cells, e.g., changes the polarization of the cellular membrane. Other changes induced by optical stimulation may include changes in cell signaling, in the actin cytoskeleton, in the cell morphology and/or volume, and in the adhesion to the cell's substrate. The cell's recovery from the state induced by the applied light stimulus is then monitored by measurements of a physical property of the sensor, such as an electrical impedance or an index of refraction.

The process of recovery is substantially influenced by the presence of certain bio-active compounds in the cell's environment, which enables some embodiments to effectively detect the presence of and/or to quantitate such compounds. In some embodiments, detection comprises acquiring a reference time series of impedance measurements determined for a standardized solution, and a target time series determined for a target sample. Differences between the two time series may indicate the presence of a bio-active analyte within the target sample.

In conventional biosensing measurements of impedance or refractive index, it may be difficult to detect small changes as are induced in a cellular membrane by the presence of a target analyte, because such small changes may be of the order of the measurement noise. In contrast to such conventional methods, some embodiments substantially boost signal-to-noise ratio by triggering relatively big changes in the cellular membrane as a result of optical stimulation, and subsequently monitoring the cell's recovery.

Compared to conventional bio-sensors using living cells, some embodiments of the present invention have several notable advantages. Among others, advantages include an increased sensitivity, which allows detection of very low analyte concentrations. Some embodiments further enable a substantial decrease of the analysis time to approximately one hour or less, compared to several hours to several days required using conventional systems and methods. Other advantages include an improved portability and susceptibility to automation.

It will be clear to one skilled in the art that the above embodiments may be altered in many ways without departing from the scope of the invention. Accordingly, the scope of the invention should be determined by the following claims and their legal equivalents.

What is claimed is:

1. A bio-sensing method comprising:
   employing a light source to deliver a pulse of light to a sensor comprising a culture of photosensitive living cells attached to a surface of an electrode;
   in response to delivering the pulse of light to the sensor, performing a target measurement of an electrical impedance of the sensor characterizing a response of the sensor to the pulse of light, the measurement performed at a time instance following a delivery of the pulse of light by a pre-determined time delay while the sensor is in contact with a target sample; and
   in response to performing the target measurement, determining whether the target sample comprises a target analyte according to a result of the target measurement and further according to a result of a reference measurement of the electrical impedance of the sensor;
   wherein the reference measurement is performed at another time instance following a delivery of another pulse of light to the sensor by the time delay, the reference measurement performed while the sensor is in contact with a reference sample.

2. The method of claim 1, comprising bringing the sensor in contact with the target sample in response to delivering the pulse of light to the sensor.

3. The method of claim 1, further comprising determining a concentration of the target analyte within the target sample according to the result of the target measurement and according to the result of the reference measurement.

4. The method of claim 3, comprising determining the concentration of the target analyte according to a difference between a first value and a second value, the first value determined according to the result of the target measurement, the second value determined according to the result of the reference measurement.

5. The method of claim 1, wherein the time delay is smaller than a recovery time required by the sensor to return to a value of the electrical impedance measured prior to the delivery of the other pulse of light while the sensor is in contact with the reference sample.

6. The method of claim 1, wherein the time delay is pre-determined according to a level of measurement noise associated with the reference measurement.

7. The method of claim 1, wherein the time delay is pre-determined according to the target analyte.

8. The method of claim 1, further comprising:
   in response to delivering the pulse of light to the sensor, performing another measurement of the electrical impedance of the sensor while the sensor is in contact with the target sample, the other measurement subsequent to the target measurement and further characterizing the response of the sensor to the pulse of light; and
   determining whether the target sample comprises the target analyte further according to a result of the other measurement.

9. The method of claim 1, further comprising, in preparation for delivering the pulse of light to the sensor:
   employing the light source to deliver the other pulse of light to the sensor; and
   in response, performing the reference measurement.

10. The method of claim 1, wherein the target measurement is performed following a termination of the pulse of light, and wherein the reference measurement is performed following a termination of the other pulse of light.

11. A system comprising:
   a sensor comprising a culture of photosensitive living cells attached to a surface of an electrode;
   a light source configured to illuminate the sensor; and
   a computer system connected to the light source and to an electrical impedance analyzer configured to measure an electrical impedance of the sensor, the computer system comprising at least one hardware processor configured to:
      actuate the light source to deliver a pulse of light to the sensor;
      in response to delivering the pulse of light, actuate the electrical impedance analyzer to perform a measurement of the electrical impedance of the sensor characterizing a response of the sensor to the pulse of light, the measurement performed at a time instance following a delivery of the pulse of light by a pre-determined time delay, the measurement performed while the sensor is in contact with a target sample; and
      in response to the target measurement, determine whether the target sample comprises a target analyte according to a result of the target measurement and further according to a result of a reference measurement of the electrical impedance of the sensor;
      wherein the reference measurement is performed at another time instance following a delivery of another pulse of light to the sensor by the time delay, the reference measurement performed while the sensor is in contact with a reference sample.

12. The system of claim 11, wherein the sensor is brought in contact with the target sample in response to delivering the pulse of light to the sensor.

13. The system of claim 11, wherein the at least one hardware processor is further configured to determine a concentration of the target analyte within the target sample according to the result of the target measurement and according to the result of the reference measurement.

14. The system of claim 13, wherein the at least one hardware processor is further configured to determine the concentration of the target analyte according to a difference between a first value and a second value, the first value determined according to the result of the target measurement, the second value determined according to the result of the reference measurement.

15. The system of claim 11, wherein the time delay is smaller than a recovery time required by the sensor to return to a value of the electrical impedance measured prior to the delivery of the other pulse of light while the sensor is in contact with the reference sample.

16. The system of claim 11, wherein the time delay is pre-determined according to a level of measurement noise associated with the reference measurement.

17. The system of claim 11, wherein the time delay is pre-determined according to the target analyte.

18. The system of claim 11, wherein the at least one hardware processor is further configured to:
  in response to actuating the light source to deliver the pulse of light to the sensor, actuate the electrical impedance analyzer to perform another measurement of the electrical impedance of the sensor while the sensor is in contact with the target sample, the other measurement subsequent to the target measurement and further characterizing the response of the sensor to the pulse of light; and
  determine whether the target sample comprises the target analyte further according to a result of the other measurement.

19. The system of claim 11, wherein the at least one hardware processor is further configured, in preparation for actuating the light source to deliver the pulse of light to the sensor, to:
  actuate the light source to deliver the other pulse of light to the sensor; and
  in response, actuate the electrical impedance analyzer to perform the reference measurement.

20. The system of claim 11, wherein the target measurement is performed following a termination of the pulse of light, and wherein the reference measurement is performed following a termination of the other pulse of light.

* * * * *